United States Patent [19]

Wissmann et al.

[11] 3,931,141
[45] Jan. 6, 1976

[54] NOVEL HEPTAPEPTIDES HAVING GASTRIN ACTIVITY

[75] Inventors: Hans Wissmann, Bad Soden, Rolf Geiger, Frankfurt am Main; Rudolf Schleyerbach, Hofheim, all of Germany

[73] Assignee: Hoechst Aktiengesellschaft, Frankfurt am Main, Germany

[22] Filed: Nov. 15, 1973

[21] Appl. No.: 416,012

[30] Foreign Application Priority Data

Nov. 17, 1972  Germany............................ 2256445

[52] U.S. Cl............................ 260/112.5 R; 424/177
[51] Int. Cl.² ................ C07C 103/52; A61K 37/00
[58] Field of Search................... 260/112.5; 424/177

[56] References Cited
UNITED STATES PATENTS
3,652,531   3/1972   Miyoshi et al. .................. 260/112.5

OTHER PUBLICATIONS
Kenner et al: J. Chem. Soc., C, 1968, pp. 761–763.

Agarwal et al: J. Chem. Soc., C, 1968, pp. 1384–1391.

Kenner, Chem. and Ind., 1972, pp. 791–794.

Wunsch et al: Hoppe–Seyler's Z. Physiol. Chem., 353, pp. 1246–1254, (1972).

Berde et al: "Neurohypophysical Hormones and Similar Polypeptides, Handbook of Experimental Pharmacology," V. 23, Eichler et al., Eds., Springer–Verlag, Berlin, 1968, pp. 856, 857, 862.

Primary Examiner—Lewis Gotts
Assistant Examiner—Reginald J. Suyat
Attorney, Agent, or Firm—Curtis, Morris & Safford

[57] ABSTRACT

Heptapeptides of the general formula

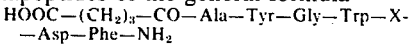

—Asp—Phe—NH₂ in which X represents leucine or methionine, and process for preparing them by reacting tert.butyl-protected heptapeptides with glutaric acid anhydride and subsequently splitting off the protective groups with the aid of trifluoroacetic acid.

4 Claims, No Drawings

NOVEL HEPTAPEPTIDES HAVING GASTRIN ACTIVITY

The present invention relates to novel heptapeptides having gastrin activity.

More particularly, the invention relates to novel heptapeptides of the general formula I HOOC—(CH$_2$)$_3$—CO—Ala—Tyr—Gly—Trp—X—Asp—Phe—NH$_2$ (I)

in which X represents leucine or methionine.

The invention also relates to a process for preparing the novel heptapeptides of the general formula I specified above, wherein peptides of the general formula II H—Ala—Tyr(Bu$^t$)—Gly—Trp—X—Asp(OBu$^t$)—Phe—NH$_2$ (II)

in which Bu$^t$ stands for the tert. butyl radical and X has the meaning given above, are reacted with glutaric acid anhydride and from the reaction products of the general formula III HOOC—(CH$_2$)$_3$—CO—Ala—Tyr(Bu$^t$)—Gly—Trp—X—Asp(OBu$^t$)—Phe—NH$_2$ (III)

the protective groups are removed by treatment with trifluoroacetic acid.

Numerous synthetic peptides which are shortened gastrinanalogs have been described which, in a similar way as is done by the natural hormone, stimulate the stomach with regard to acid production and the quantity secreted. Among these synthetic peptides, the pentapeptide of the formula IV Boc—β—Ala—Trp—Met—Asp—Phe—NH$_2$ (IV)

in which Boc stands for the tert. butyloxycarbonyl group (The Lancet 1966, page 933) is outstanding and shows the strongest stimulating action, compared with that of other synthetic peptides.

With this pentapeptide IV, a heptapeptide has been compared which differs from the compound of the invention of the formula I with X = Met in that it does not contain the glutaroyl group. It has a biological action which is comparable to that of the peptide IV.

In contradistinction thereto, the peptide of the formula I of the invention, in which X stands for methionine, has a 1.3-fold stronger biological action than the peptide of the formula IV and the peptide of the invention of the formula I with X = leucine even has a 3-fold stronger biological activity than the peptide of the formula IV, calculated on molar basis.

The biological activity was determined in a perfused stomach of the rat according to Brit. J. Pharmacol. 38 (1970), pages 206–213.

For preparing the compounds of the general formula I, the peptides of the formula II are reacted with glutaric acid anhydride in dimethylformamide, reaction times of about 4 – 20 hours at 0° – 5° C being sufficient. The solvent is removed by distillation under reduced pressure and the residue is triturated with ether. The reactive groups are split off with 90% trifluoroacetic acid at room temperature (reaction time about 1 hour). For purifying the peptides of the general formula I, it is sufficient, for example, to dissolve and reprecipitate them in a mixture of alcohol and ether.

The novel peptides of the invention are medicaments. They are free from non-physiological components, serve for the stimulation of the production of gastric juice and may be used as diagnostic agents in function tests of the stomach or as therapeutic agents in the case of reduced secretion of gastric juice in the stomach, gall and pancreas.

The form for parenteral adminstration is a 0.001 to 0.1% aqueous solution, if desired with the addition of physiological amounts of sodium chloride or in a buffered aqueous solution. As buffer there may be used, for example: m/15 phosphate buffer (primary potassium phosphate and secondary sodium phosphate according to Sörensen and Clark) with pH-values of 5.0 to 7.5. These solutions serve for subcutaneous and intramuscular injections.

For nasal application, about 0.1% aqueous solutions, 0.1 to 3% oily suspensions or a 0.1 to 3% dry powder, for example with lactose or mannite as carrier, may be used.

The following Examples illustrate the invention:

EXAMPLES

For the purity tests of the compounds prepared as described in the following Example, thin-layer chromatography was used with the following solvent systems:
1. tert.Butanol/pyridine/petroleum ether, 1:1:8
2. Methanol/water, 80:20
3. Methylethylketone/pyridine/water/glacial acetic acid, 70:15:15:2
4. Butanol/acetic acid/water, 2:1:1.

The abbreviations usual in peptide chemistry are used; dicyclohexyl-carbodiimide = DCC; dimethylformamide = DMF.

EXAMPLE 1

Glutaroyl—Ala—Tyr—Gly—Trp—Leu—Asp—Phe—NH$_2$ a. Z—Tyr(Bu$^t$)—Gly—OCH$_3$ 74 g (0.2 mole) of Z—Tyr(OBu$^t$)—OH and 54 g (0.4 mole) of 1-hydroxybenzotriazole were dissolved in 300 ml of tetrahydrofurane, the whole was cooled to −5° C and then combined with the solution of 42 g (0.2 mole) of DCC in 50 ml of tetrahydrofurane. The mixture was stirred for 1 hour at 0° C and for 1 hour at room temperature. The dicyclohexyl-urea that had separated was removed by suction-filtration. The remaining solution was combined at 0° C with a solution of 25 g (0.2 mole) of glycinemethyl ester-hydrochloride and 27 ml (0.2 mole) of N-ethylmorpholine in 150 ml of tetrahydrofurane. The solution was stirred for 2 hours at room temperature, the solvent was removed by distillation under reduced pressure at room temperature, the residue was dissolved in ethyl acetate and the ethyl acetate solution was shaken with 0.2N-sulfuric acid, a saturated sodium bicarbonate solution and water. After the ethyl acetate solution was dried over magnesium sulfate, the final product was obtained by removal of the solvent by distillation under reduced pressure in the form of a weakly yellowish oil. Thin-layer chromatography showed the product to be uniform in the systems 1, 2, 3 and 4.

Yield: 64 g (73% of the theory).

b. H—Tyr(Bu$^t$)—Gly—OCH$_3$ . HCl 60 g of Z—Tyr(Bu$^t$)—Gly—OMe in 1 liter of methanol were hydrogenated catalytically at pH 3 with 10 g of 10% Pd/SO$_4$ with the addition of 1N-methanolic HCl. After the catalyst was separated, the solvent was removed by distillation. The remaining resin solidified upon trituration with ether.

Yield: 45 g, melting point: from 97° C onwards, under foaming. [α]$_D^{20}$: + 27.0° (c = 1, in methanol).

c. Z—Ala—Tyr(Bu$^t$)—Gly—OCH$_3$ 29 g of DCC were added at 5° C to a solution of 29 g (0.13 mole) of Z—Ala—OH and 35 g of 1-hydroxybenzotriazole in 240 ml of DMF. The whole was stirred for 1 hour at 0° C and for 1 hour at room temperature; the dicyclohexyl-urea that had precipitated was filtered off and a solution of 44.8 g (0.13 mole) of H—Tyr(Bu$^t$)—Gly—OCH$_3$, HCl and 16.5 ml of N-ethyl-morpholine in 300 ml of DMF was added. After a reaction time of 3 hours at room temperature, the solvent was removed by distillation under reduced pressure, the residue was dissolved in ethyl acetate and the ethyl acetate solution was washed with 1N—HCl, saturated sodium bicarbonate and water, dried over sodium sulfate and evaporated under reduced pressure. The semi-solid reaction product solidified upon digestion with ether.

Yield: 46.5 g (70%); melting point 107° C. $[\alpha]_D^{20}$ = −34.9° (c = 1, in methanol).

C$_{27}$H$_{35}$N$_3$O$_7$(513) Calc.: C, 63.1; H, 6.8; N, 8.2. Found: C, 63.4; H, 6.9; N, 8.1.

In thin-layer chromatography, the product was found to be uniform in the systems 1 and 2.

d. Z—Ala—Tyr(Bu$^t$)—Gly—OH 44.6 g of the methyl ester obtained according to (c) were stirred for 1 hour at room temperature in 150 ml of dioxane and 89 ml of 1N-sodium hydroxide solution. The mixture was neutralized with 1N—HCl, evaporated under reduced pressure to one third of its original volume and adjusted to pH 3 with 1N—HCl. The oil that had separated was dissolved in 700 ml of ether. The solution was dried over MgSO$_4$ and combined with 250 ml of petroleum ether. The precipitate crystallized within some days at 0° C.

Yield: 37.4 g (88%); melting point 89° C. $[\alpha]_D^{20}$ = −42.7° (c = 1 in methanol).

In thin-layer chromatography, the product was found to be uniform in the systems 1 and 2.

e. Z—Trp—Leu—OH 83. g of Z—Trp—Leu—OMe, prepared according to J. Org. Chem. 31 (1966), page 3400, were stirred in a mixture of 500 ml of dioxane and 100 ml of 2N—NaOH for 100 minutes. The pH was adjusted to 6 with the aid of 1N—HCl, the mixture was concentrated, combined with a small amount of water and the pH was adjusted to 3 with the aid of 1N—HCl. The product that had precipitated was recrystallized from a mixture of methanol and water.

Yield: 72.5 g, melting point 70° C, $[\alpha]_D^{20}$ = −27.5° (c = 1, in methanol).

f. Z—Trp—Leu—Asp(OBu$^t$)—Phe—NH$_2$

A solution of 10.8 g of DCC in 18 ml of tetrahydrofurane was added, at −5° C, while stirring, to a solution of 23.8 g (52 mmoles) of Z—Trp—Leu—OH, 19.5 g (52 mmoles) of H—Asp(OBu$^t$)—Phe—NH$_2$.HCl, prepared according to J. Chem. Soc. (C) 1966, page 555, 12 g of N-hydroxysuccinimide and 6.65 ml of N-ethylmorpholine in 400 ml of tetrahydrofurane. The temperature of the reaction mixture was allowed to rise to room temperature, while stirring. The mixture was allowed to stand overnight, the dicyclohexylurea that had precipitated was filtered off and the solution was dried under reduced pressure. The remaining oil was saturated with 5% citric acid, digested with sodium bicarbonate and water, dried over P$_2$O$_5$ under reduced pressure and boiled with a small amount of ethanol.

Yield: 31.5 g, melting point 212° C, $[\alpha]_D^{20}$ = −36.7° (c = 1, in DMF).

In thin-layer chromatography, the product was found to be uniform in the systems 1, 2, 3 and 4.

g. H—Trp—Leu—Asp(OBu$^t$)—Phe—NH$_2$, HCl 7.68 g of Z-tetrapeptide were hydrogenated catalytically in 350 ml of methanol in a manner analogous to that described in Example 1(b). After the usual working up, 6.5 g of an amorphous product were obtained. $[\alpha]_D^{20}$ = −22° (c = 1, in methanol).

The product was found to be uniform in thin-layer chromatography in the systems 1, 2, 3 and 4.

h. Z—Ala—Tyr(Bu$^t$)—Gly—Trp—Leu—Asp—(OBu$^t$)—Phe—NH$_2$ 0.5 g (1 mmole) of Z—Ala—Tyr(Bu$^t$)—Gly—OH, 0.64 g (1 mmole) of H—Trp—Leu—Asp(OBu$^t$)—Phe—NH$_2$.HCl, prepared from the Z-compound by catalytic hydrogenation (Example g), 0.27 g (2 mmoles) of 1-hydroxybenzotriazole and 0.13 ml of N-ethyl-morpholine were dissolved in 10 ml of DMF, combined at 0° C with 0.24 g of DCC and stirred for 15 hours at room temperature. The dicyclohexylurea that had separated was filtered off and the solution was concentrated under reduced pressure. The residue was dissolved in ethyl acetate and extracted at a temperature below 5° C with 10% citric acid, then washed at room temperature with saturated sodium bicarbonate and water. After the ethyl acetate solution was dried over MgSO$_4$, it was concentrated. Thereupon, 450 mg of the Z-heptapeptide precipitated. A further 193 mg could be isolated from the mother liquor by precipitation with ether. Melting point 192° C. $[\alpha]_D^{20}$ = −27.8° (c = 1, in DMF).

Amino-acid analysis: Asp 1.0, Gly 0.99, Ala 1.02 Leu 0.98, Tyr 0.90, Phe 0.99 Tyr/Trp = 1.03

In thin-layer chromatography, the product was found to be uniform in the systems 1, 3 and 4.

i. H—Ala—Tyr(Bu$^t$)—Gly—Trp—Leu—Asp(OBu$^t$)—Phe—NH$_2$, NCl 4 g of Z-heptapeptide were hydrogenated catalytically in 1.3 liter of methanol in a manner analogous to that described in Example 1(b). After the solvent had been removed by distillation, the residue was digested with ether, whereupon 2.8 g of product melting at 199° − 200° C (decomposition) were obtained.

k. Glutaroyl—Ala—Tyr(Bu$^t$)—Gly—Trp—Leu—Asp—OBu$^t$)—Phe—NH$_2$ 2.3 g (20 mmoles) of glutaric acid anhydride and 2.56 ml of N-ethylmorpholine were introduced portionwise at 0° C, while stirring, into a solution of 8.8 g (12 mmoles) of the H-heptapeptide hydrochloride in 50 ml of DMF, within 40 minutes. The whole was stirred for 5 hours at 0° C and allowed to stand for 16 hours at 4° C. The solvent was then removed by distillation under reduced pressure and the residue was digested with ether.

Yield: 8.8 g, melting point 230° − 232° C (decomposition). $[\alpha]_D^{20}$ = −31° (c = 1, in DMF).

l. Glutaroyl—Ala—Tyr—Gly—Trp—Leu—Asp—Phe—NH$_2$ 1.27 g of the protected glutaroyl-heptapeptide were stirred for 90 minutes at room temperature in 5 ml of 90% trifluoroacetic acid. The trifluoroacetic acid was then removed by distillation under reduced pressure and the residue was digested with ether and reprecipitated from a mixture of ethanol and ether.

Yield: 620 mg, melting point 213° C (decomposition). $[\alpha]_D^{20}$ = −33.8° (c = 1, in DMF).

Amino-acid analysis: Asp 1.09, Gly 1.00, Ala 1.07, Leu 1.08, Tyr 0.69, Phe 1.02 Tyr/Trp = 1.02

In thin-layer chromatography, the product was found to be uniform in the systems 2, 3 and 4.

EXAMPLE 2

Glutaroyl-Ala-Tyr-Gly-Trp-Met-Asp-Phe-NH₂ a. Z—Ala—Tyr—(Buᵗ)—Gly—Trp—Met—Asp—(OBuᵗ)—Phe—NH₂

17.7 g of Z—Ala—Tyr(Buᵗ)—Gly—OH, prepared according to Example 1 (d), 23 g of H—Trp—Met—Asp(OBuᵗ)—Phe—NH₂, prepared according to J. Chem. Soc. (C), 1967, page 2410, and 9.6 g of 1-hydroxy-benzotriazole were dissolved in 120 ml of DMF. 8 g of DCC were added at 0° C and the whole was stirred overnight at room temperature. After the dicyclohexyl-urea had been removed by filtration, the solution was concentrated under reduced pressure, the residue was triturated with water, 0.2N—HCl, saturated sodium bicarbonate and water and dried under a high vacuum over $P_2O_5$.

Yield: 37.3 g, melting point 228° C. $[\alpha]_D^{20} = -27.9°$ (c = 1, in DMF).

$C_{59}H_{75}N_9O_{12}S$ (1133) Calc.: C, 62.5; H, 6.62; N, 11.1; S, 2.82. Found: C, 62.6; H, 6.7; N, 11.1; S, 2.9.

b. H—Ala—Tyr(Buᵗ)—Gly—Trp—Met—Asp(OBuᵗ)—Phe—NH₂

37 g of the Z-heptapeptide were hydrogenated catalytically in 400 ml of DMF with the addition of 15 ml of cyclohexylamine and a large amount of Pd. When the splitting off of the Z-group was completed, the catalyst was removed by filtration, the solution was dried under reduced pressure and the residue was triturated with ether. For further purification, the product was precipitated from a mixture of DMF/ether/petroleum ether.

Yield: 24.3 g, melting point 209° C (Z), $[\alpha]_D^{20} = -22.5°$ (c = 1, in DMF).

c. Glutaroyl—Ala—Tyr(Buᵗ)—Gly—Trp—Met—Asp(OBuᵗ)—Phe—NH₂

3 g of glutaric acid anhydride and 4.3 ml of N-ethylmorpholine were added portionwise, at 0° C, while stirring, within 40 minutes, to a solution of 12 g of the H-heptapeptide in 60 ml of DMF. Stirring was continued for 5 hours at 0° C and the whole was allowed to stand for 16 hours at 4° C. The solvent was then removed by distillation under reduced pressure and the residue was digested with ether.

Yield: 10.3 g, melting point 231° C (decomposition), $[\alpha]_D^{20} = -31°$ (c = 1, in DMF).

d. Glutaroyl—Ala—Tyr—Gly—Trp—Met—Asp—Phe—NH₂

10.1 g of the protected glutaroyl heptapeptide were dissolved in 50 ml of 90% trifluoroacetic acid. After the whole had been allowed to stand for 75 minutes at room temperature, the trifluoroacetic acid was removed by distillation under reduced pressure. The residue was digested with 10 ml of ethanol and the combined with 100 ml of ether. For purification, the product was reprecipitated from a mixture of methanol and ether.

Yield: 9.65 g, melting point 216° C, $[\alpha]_D^{20} = -31.2°$ ( c = 1, in DMF).

Amino-acid analysis: Asp 0.96, Gly 0.94, Ala 0.93, Met 0.85, Tyr 0.99, Phe 1.00. Tyr/Trp = 1.04.

We claim:

1. A heptapeptide of the formula
   HOOC—(CH₂)₃—CO—Ala—Tyr—Gly—Trp—X—
   —Asp—Phe—NH₂,
   wherein X is leucine (Leu) or methionine (Met) and the optically-active amino acids are L-amino acids.

2. A heptapeptide as defined in claim 1 in which X represents leucine (Leu).

3. A heptapeptide as defined in claim 1 in which X represents methionine (Met).

4. A method for making a heptapeptide of the formula
   HOOC—(CH₂)₃—CO—Ala—Tyr—Gly—Trp—X—
   —Asp—Phe—NH₂,
   wherein the optically-active amino acids are L-amino acids and wherein X is leucine (Leu) or methionine (Met), which method comprises reacting glutaric acid anhydride with a peptide wherein the optically-active amino acids are L-amino acids, said peptide having the formula
   H—Ala—Tyr(Buᵗ)—Gly—Trp—X—Asp(OBuᵗ)—
   Phe—NH₂,
   wherein Buᵗ is tert. butyl, to form a reaction product of the formula
   HOOC—(CH₂)₃—CO—Ala—Tyr(Buᵗ)—Gly—Trp—X—Asp(OBuᵗ)—Phe—NH₂,
   wherein the optically-active amino acids are L-amino acids, and then treating said reaction product with trifluoroacetic acid to remove the protective tert. butyl groups.

* * * * *